United States Patent
Overmyer (10) Patent No.: US 10,702,349 B2
(45) Date of Patent: Jul. 7, 2020

(54) ROBOTIC SURGICAL INSTRUMENT COMMUNICATION

(71) Applicant: Ethicon LLC, Guaynabo, PR (US)

(72) Inventor: Mark D. Overmyer, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 320 days.

(21) Appl. No.: 15/900,096

(22) Filed: Feb. 20, 2018

(65) Prior Publication Data

US 2019/0254762 A1 Aug. 22, 2019

(51) Int. Cl.
| | | |
|---|---|---|
| *A61B 34/35* | (2016.01) | |
| *A61B 17/00* | (2006.01) | |
| *A61B 17/072* | (2006.01) | |
| *A61B 34/37* | (2016.01) | |
| *A61B 34/30* | (2016.01) | |
| *A61B 90/00* | (2016.01) | |

(Continued)

(52) U.S. Cl.
CPC ........ *A61B 34/35* (2016.02); *A61B 17/00234* (2013.01); *A61B 17/07207* (2013.01); *A61B 34/37* (2016.02); *A61B 18/1445* (2013.01); *A61B 90/98* (2016.02); *A61B 2017/00017* (2013.01); *A61B 2017/00022* (2013.01); *A61B 2017/00026* (2013.01); *A61B 2017/00221* (2013.01); *A61B 2017/00296* (2013.01); *A61B 2017/00477* (2013.01); *A61B 2017/07271* (2013.01); *A61B 2017/07285* (2013.01); *A61B 2017/2927* (2013.01); *A61B 2018/00595* (2013.01); *A61B 2034/301* (2016.02); *A61B 2090/064* (2016.02); *A61B 2090/066* (2016.02); *A61B 2090/067* (2016.02)

(58) Field of Classification Search
CPC ................................ A61B 34/35; A61B 17/00
See application file for complete search history.

(56) References Cited

U.S. PATENT DOCUMENTS

| 5,558,671 A | 9/1996 | Yates |
|---|---|---|
| 7,143,925 B2 | 12/2006 | Shelton, IV et al. |

(Continued)

FOREIGN PATENT DOCUMENTS

| EP | 2923653 A2 | 9/2015 |
|---|---|---|
| WO | WO-2014151621 A1 | 9/2014 |
| WO | WO-2014151952 A1 | 9/2014 |

OTHER PUBLICATIONS

U.S. Appl. No. 15/422,740 entitled "Resisting Torque in Articulating Surgical Tools" filed Feb. 2, 2017.

(Continued)

*Primary Examiner* — Kira Nguyen
(74) *Attorney, Agent, or Firm* — Mintz Levin Cohn Ferris Glovsky and Popeo, P.C.

(57) ABSTRACT

Various exemplary methods, systems, and devices for robotic surgical instrument communication are provided. In general, a surgical tool includes a sensor configured to sense a parameter related to the surgical tool and to wirelessly communicate the sensed data to another device, e.g., another surgical tool. Each of the surgical tool and the other device are configured to be operatively connected to a robotic surgical system and to be controlled by the robotic surgical system. The other device is configured to transmit the data received from the surgical tool to the robotic surgical system.

20 Claims, 5 Drawing Sheets

(51) Int. Cl.
    *A61B 90/98*     (2016.01)
    *A61B 18/00*     (2006.01)
    *A61B 18/14*     (2006.01)
    *A61B 17/29*     (2006.01)

(56) References Cited

U.S. PATENT DOCUMENTS

| | | | |
|---|---|---|---|
| 8,317,070 B2 | 11/2012 | Hueil et al. | |
| 8,393,514 B2 | 3/2013 | Shelton, IV et al. | |
| 8,512,318 B2* | 8/2013 | Tovey | A61B 34/76 606/1 |
| 9,943,377 B2 | 4/2018 | Yates et al. | |
| 2008/0211634 A1* | 9/2008 | Hopkins | A61B 17/32002 340/10.1 |
| 2011/0119224 A1* | 5/2011 | Mangione-Smith | A61B 6/12 706/52 |
| 2011/0295269 A1 | 12/2011 | Swensgard et al. | |
| 2012/0292367 A1 | 11/2012 | Morgan et al. | |
| 2013/0256377 A1 | 10/2013 | Schmid et al. | |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1 | 5/2015 | Shelton, IV et al. | |
| 2015/0134077 A1 | 5/2015 | Shelton, IV et al. | |
| 2015/0209059 A1 | 7/2015 | Trees et al. | |
| 2015/0209573 A1 | 7/2015 | Hibner et al. | |
| 2015/0272575 A1 | 10/2015 | Leimbach et al. | |
| 2015/0351758 A1 | 12/2015 | Shelton, IV et al. | |
| 2016/0270780 A1 | 9/2016 | Hall et al. | |
| 2018/0000543 A1 | 1/2018 | Hibner | |
| 2018/0049629 A1* | 2/2018 | Nakagawa | A61B 1/00009 |
| 2018/0049813 A1 | 2/2018 | Yates et al. | |
| 2018/0110402 A1* | 4/2018 | Yamada | A61B 1/0638 |

OTHER PUBLICATIONS

U.S. Appl. No. 15/689,072 entitled "Methods, Systems and Devices for Controlling Electrosurgical Tools" filed Aug. 29, 2017.
International Search Report and Written Opinion for PCT/IB2019/050309 dated Jun. 18, 2019 (25 pages).

\* cited by examiner

ROBOTIC SURGICAL INSTRUMENT COMMUNICATION

FIELD

The present disclosure relates generally to robotic surgical instrument communication.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

In general, methods, systems, and devices for robotic surgical instrument communication are provided.

In one aspect, a surgical system is provided that in one embodiment includes a surgical tool including an elongate shaft having an end effector at a distal end thereof. The end effector is configured to be disposed within a body of a patient. The surgical tool is configured to releasably and replaceably couple to a robotic surgical system configured to provide a control signal to the surgical tool to allow the end effector to perform a function. The surgical tool includes a sensor at the end effector. The sensor is configured to sense a parameter associated with the surgical tool, and the sensor is configured to wirelessly transmit a signal indicative of the sensed parameter to a second surgical tool disposed within the body of the patient and releasably and replaceably coupled to the robotic surgical system.

The surgical system can have any of a number of variations. For example, the parameter associated with the surgical tool can include at least one of force, pressure, type of a staple cartridge seated in the end effector, presence of a staple cartridge within the end effector, impedance of tissue engaged by the end effector, position of a cutting element of the surgical tool relative to the end effector, and angle of the end effector relative to the elongate shaft. For another example, the function can include at least one of closing the end effector, opening the end effector, articulating the end effector relative to the elongate shaft, rotating the end effector relative to the elongate shaft, rotating the end effector and the elongate shaft as a unit about a longitudinal axis of the elongate shaft, ejecting staples from the end effector, and applying energy to tissue engaged by the end effector.

For yet another example, the surgical system can include a second surgical tool configured to be disposed within the body of the patient, configured to releasably and replaceably couple to the robotic surgical system, including a communication mechanism configured to receive the signal from the sensor, and configured to transmit a second signal indicative of the signal to the robotic surgical system. In at least some embodiments, the communication mechanism can include a transceiver, and the second surgical tool can include a wire operatively connected to the communication mechanism, extending along an elongate shaft of the second surgical tool, and configured to communicate the second signal. In at least some embodiments, the communication mechanism can include an antenna, and the second surgical tool can include a circuit board configured to process the signal received by the antenna into the second signal. In at least some embodiments, the second surgical tool can include a camera. In at least some embodiments, the surgical system can include a control system of the robotic surgical system configured to receive the second signal from the second surgical tool, and the control system can be configured to use the second signal to generate the control signal.

In another embodiment, a surgical system includes a first surgical tool and a second surgical tool. The first surgical tool includes an elongate shaft having an end effector at a distal end thereof. The end effector is configured to be disposed within a body of a patient. The surgical tool is configured to releasably and replaceably couple to a robotic surgical system configured to provide a control signal to the surgical tool to allow the end effector to perform a function. The surgical tool includes a sensor at the end effector, and the sensor is configured to sense a parameter associated with the surgical tool. The second surgical tool is configured to be disposed within the body of the patient and to be releasably and replaceably coupled to the robotic surgical system. The second surgical tool is configured to wirelessly receive a first signal from the first surgical tool that is indicative of the sensed parameter, and the second surgical tool is configured to transmit a second signal indicative of the first signal to the robotic surgical system.

The surgical system can have any of a variety of variations. For example, the parameter associated with the first surgical tool can include at least one of force, pressure, type of a staple cartridge seated in the end effector, presence of a staple cartridge within the end effector, impedance of tissue engaged by the end effector, position of a cutting element of the surgical tool relative to the end effector, and angle of the end effector relative to the elongate shaft. For another example, the function can include at least one of closing the end effector, opening the end effector, articulating the end effector relative to the elongate shaft, rotating the end effector relative to the elongate shaft, rotating the end effector and the elongate shaft as a unit about a longitudinal axis of the elongate shaft, ejecting staples from the end effector, and applying energy to tissue engaged by the end effector. For yet another example, the second surgical tool can include a communication mechanism configured to receive the first signal from the first surgical tool, and the communication mechanism can include a transceiver. For still another example, the second surgical tool can include a communication mechanism configured to receive the first signal from the first surgical tool, the communication mechanism can include an antenna, and the second surgical tool can include a circuit board configured to process the signal received by the antenna into the second signal. For another example, the second surgical tool can include a camera. For still another example, the surgical system can include a control system of the robotic surgical system configured to receive the second signal from the second surgical tool, and the control system can be configured to use the second signal to generate the control signal.

In another aspect, a surgical method is provided that in one embodiment includes positioning an end effector of a first surgical tool in a body of a patient. The first surgical tool is releasably and replaceably coupled to a robotic surgical system. The surgical method also includes positioning a distal portion of a second surgical tool in the body of the patient. The second surgical tool is releasably and replaceably coupled to the robotic surgical system. The surgical method also includes sensing a parameter associated with the first surgical tool with a sensor at the end effector of the first surgical tool, and wirelessly transmitting a first signal from the end effector of the first surgical tool to a communication mechanism at the distal portion of the second surgical tool. The first signal is indicative of the sensed parameter. The surgical method also includes transmitting a second signal from the second surgical tool to the robotic surgical system. The second signal is indicative of the first signal received by the second surgical tool.

The surgical method can vary in any number of ways. For example, the surgical method can include transmitting a third signal from the robotic surgical system to the first surgical tool based on the second signal received by the robotic surgical system, and the third signal can include an instruction to the first surgical tool for performance of a function of the end effector. In at least some embodiments, the function can include at least one of closing the end effector, opening the end effector, articulating the end effector relative to the elongate shaft, rotating the end effector relative to the elongate shaft, rotating the end effector and the elongate shaft as a unit about a longitudinal axis of the elongate shaft, ejecting staples from the end effector, and applying energy to tissue engaged by the end effector.

For another example, the parameter associated with the first surgical tool can include at least one of force, pressure, type of a staple cartridge seated in the end effector, presence of a staple cartridge within the end effector, impedance of tissue engaged by the end effector, position of a cutting element of the surgical tool relative to the end effector, and angle of the end effector relative to the elongate shaft.

For yet another example, the transmission of the second signal can include transmission of the second signal along a wire extending along an elongate shaft of the second surgical tool.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Various exemplary methods, systems, and devices for robotic surgical instrument communication are provided. In general, a surgical tool includes a sensor configured to sense a parameter related to the surgical tool and to wirelessly communicate the sensed data to another device, e.g., another surgical tool. Each of the surgical tool and the other device are configured to be operatively connected to a robotic surgical system and to be controlled by the robotic surgical system. The other device is configured to transmit the data received from the surgical tool to the robotic surgical system, thereby allowing the robotic surgical system to use the data to more effectively control the surgical tool.

In an exemplary embodiment, the surgical tool is an endoscopic surgical tool that has an elongate shaft and an end effector at a distal end of the shaft. The elongate shaft of an endoscopic surgical tool typically has a relatively small diameter to facilitate its minimally invasive use, which results in a limited amount of space available in the shaft for components necessary to accomplish various functions of the end effector, such as any one or more of articulation of the end effector, opening and closing of the end effector, ejection of staples from the end effector, application of energy to tissue engaged by the end effector, rotation of the end effector about a longitudinal axis of the shaft, and other end effector functions. The surgical tool's sensor can be located at the end effector, but in at least some cases there is insufficient real estate within the tool's shaft for wires and/or other physical equipment necessary to allow the sensor's sensed data to be communicated to the robotic surgical tool from the surgical tool. Additionally, wireless communication from an end effector disposed within a patient's body is often unreliable, if not ineffective entirely, because it can be difficult for wireless signals to pass from within the patient's body through the patient's body wall. Allowing the surgical tool to communicate with another device may avoid these difficulties by allowing the surgical tool to communicate with another device located within the same patient as the surgical tool. In an exemplary embodiment, the other device has a larger diameter elongate shaft than the surgical tool and can thus more easily accommodate wires and/or other physical equipment necessary to allow data to be communicated to the robotic surgical tool from the device, and/or the other device can have fewer and/or smaller components within its elongate shaft than the surgical tool such that the device can more easily accommodate wires and/or other physical equipment necessary to allow data to be communicated to the robotic surgical tool from the device. The surgical tool does not need to include any wires or other physical components within its shaft to allow for communication with the other device, thereby allowing other components to occupy this valuable, limited shaft space.

In an exemplary embodiment, the other device with which the surgical tool is configured to communicate is an endoscopic camera. Endoscopic procedures typically use a camera throughout the procedure to provide visualization of the surgical space to a surgeon and/or other medical personnel. The camera may thus be consistently available within a patient for communication with a surgical tool disposed within the patient. The other device can, however, be another type of device.

Figure 1:
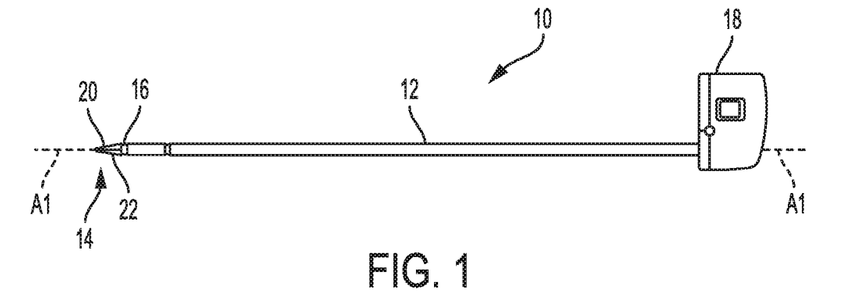
FIG. 1 is a side schematic view of one embodiment of a surgical tool.

FIG. 1 illustrates one embodiment of a surgical tool 10 that includes an elongate shaft 12, an end effector 14, a wrist 16 that couples the end effector 14 to the shaft 12 at a distal end of the shaft 12, and a tool housing 18 coupled to a proximal end of the shaft 12. The end effector 14 is configured to move relative to the shaft 12 at the wrist 16, e.g., by pivoting at the wrist 16, to position the end effector 14 at a desired location relative to a surgical site during use of the tool 10. In other embodiments, however, the end effector 14 may be in a fixed position relative to the shaft 12. The housing 18 includes various components (e.g., gears and/or actuators) configured to control the operation various features associated with the end effector 14 (e.g., any one or more of clamping, firing, rotation, articulation, energy delivery, etc.). In at least some embodiments, the shaft 12, and hence the end effector 14 coupled thereto, is configured to rotate about a longitudinal axis A1 of the shaft 12. In such embodiments, the various components of the housing 18 are configured to control the rotational movement of the shaft 12. The surgical tool 10 is configured to releasably couple to a robotic surgical system, and the tool housing 18 can include coupling features configured to allow the releasable coupling of the tool 10 to the robotic surgical system. Each of the shaft 12, end effector 14, wrist 16, and housing 18 are discussed further below.

The surgical tool 10 can have any of a variety of configurations. In general, the surgical tool can be configured to perform at least one surgical function and can include any of, for example, forceps, a grasper, a needle driver, scissors, an electrocautery tool that applies energy, a stapler, a clip applier, a suction tool, an irrigation tool, an imaging device (e.g., an endoscope or ultrasonic probe), etc. The surgical tool 10 in at least some embodiments is configured to apply energy (such as radiofrequency (RF) energy) to tissue, while in other embodiments the tool 10 is not configured to apply energy to tissue.

The shaft 12 can have any of a variety of configurations. In general, the shaft 12 is an elongate member extending distally from the housing 18 and having at least one inner lumen extending therethrough. The shaft 12 is fixed to the housing 18, but in other embodiment the shaft 12 can be releasably coupled to the housing 18 such that the shaft 12 can be interchangeable with other shafts. This may allow a single housing 18 to be adaptable to various shafts having different end effectors.

The end effector 14 can have a variety of sizes, shapes, and configurations. The end effector 14 in this illustrated embodiment includes a tissue grasper having a pair of opposed jaws 20, 22 configured to move between open and closed positions with one or both of the jaws 20, 22 configured to pivot at the wrist 16 to move the end effector 14 between the open and closed positions. The end effector 14 in other embodiments can have other configurations, e.g., scissors, a babcock, a retractor, etc.

Figure 2:
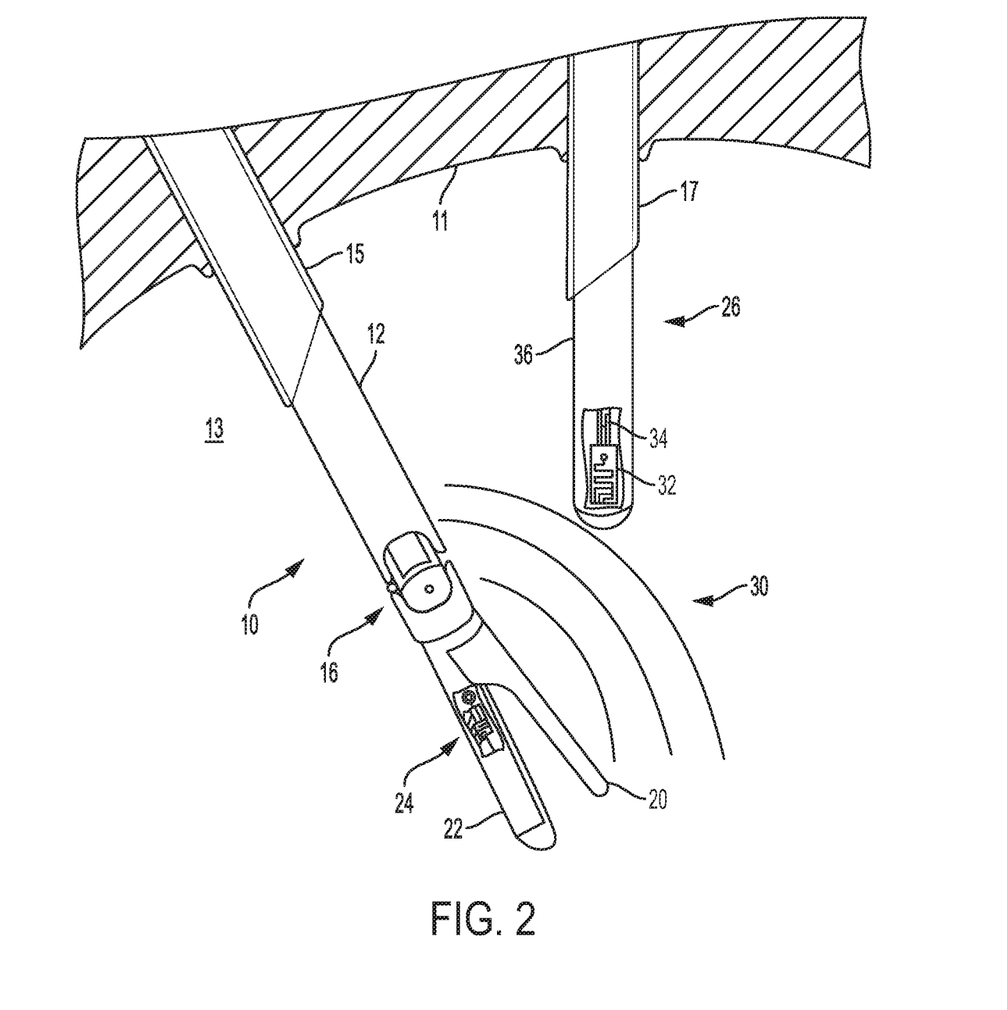
FIG. 2 is a perspective view of a distal portion of the surgical tool of FIG. 1 and a distal portion of a second surgical tool positioned in a body cavity.

As shown in FIG. 2, the end effector 14 has a sensor 24 configured to sense a parameter related to the tool 10 and to wirelessly communicate the sensed data to another device. The sensor 24 at the end effector 14 is obscured in FIG. 1. Examples of parameters that the sensor 24 can be configured to sense include use status of the tool 10, force or torque, pressure, type of staple cartridge seated in the end effector 14 (when the tool 10 is a stapler), presence of a staple cartridge within the end effector 14 (when the tool 10 is a stapler), impedance of tissue grasped by the jaws 20, 22, position of a cutting element relative to the end effector 14, and angle of the end effector's jaws 20, 22. The end effector 14 can have a single sensor or can have multiple sensors, in which case each of the multiple sensors can be configured to sense a different parameter.

The sensor 24 is configured to wirelessly communicate the sensed data to another device, such as a second surgical tool 26 disposed in the same patient as the surgical tool 10. The wireless communication can be achieved using any of a variety of wireless communication techniques, as will be appreciated by a person skilled in the art, such as Bluetooth, Wi-Fi, radio frequency identification (RFID), etc. The sensor 24 in this illustrated embodiment includes both sensing and communication capabilities, but in other embodiments, the surgical tool 10 can have a sensor with sensing capability and a communication unit with wireless communication capability. The communication unit in such an embodiment is configured to receive sensed data from the sensor and to communicate the sensed data wirelessly from the surgical tool to another device. The sensor 24 having both sensing and communication capabilities may help facilitate manufacturing of the sensor 24 and/or may help reduce a size of the sensor 24 and thus make the sensor 24 easier to retrofit into an existing surgical tool or to incorporate into a surgical tool during manufacturing, as compared to a surgical tool having a sensor for sensing and a communication unit for communicating. The sensor 24 can include a power source, e.g., a coin cell battery or other type of battery, etc.

Wireless communication is depicted in FIG. 2 with wireless signal lines 30 from the surgical tool 10 to the second surgical tool 26. The second surgical tool 26 includes a communication mechanism 32 configured to receive the wireless signal from the sensor 24. In at least some embodiments, the communication mechanism 32 can be configured to provide power to the sensor 24 of the surgical tool 10, which may help reduce a size of the sensor 24. The communication mechanism 32 can have a variety of configurations. For example, the communication mechanism 32 can include a transceiver configured to receive wireless signals from the surgical tool 10, e.g., the sensor 24 thereof, and convert them into electrical signals that can be transmitted along a wire 34 and to the robotic surgical system. For another example, the communication mechanism 32 can include a passive antenna, and the second surgical tool 26 can have a circuit board at its proximal end, e.g., within the second surgical tool's tool housing, that is operatively connected to the antenna via a wire. The circuit board can be configured to translate the wireless signals received by the antenna and parse them into signals for transmission to the robotic surgical system.

The other device, e.g., the second surgical tool 26, is configured to communicate the data received from the surgical tool 10 to a robotic surgical system to which the surgical tool 10 and the other device are each operatively connected. The other device can communicate the data to the robotic surgical system via a wired connection, which may facilitate reliable transmission of the sensed data to the robotic surgical system. The second surgical tool 26 in this illustrated embodiment has a wire 34 extending along an elongate shaft 36 of the tool 26. The wire 34 operatively connects to the robotic surgical system, such as via a tool housing (not shown) at the proximal end of the second surgical tool 26. The robotic surgical system may use the data received from the other device in controlling the surgical tool 10.

For example, when the parameter sensed by the sensor 24 is force or torque being applied to the end effector 14, such as force or torque a cutting element translating along the end effector 14 to cut tissue grasped by the end effector 14 or force or torque from external material pressing against the end effector 14 within a patient's body, the robotic surgical system can use the force or torque data to adjust the end effector 14, e.g., the articulation angle thereof, the rotational position thereof, etc., to improve control of the tool 10, such as so the end effector 14 remains within safe operating conditions, the force or torque being applied to the end effector 14 is countered to allow the end effector 14 to remain at a desired position, etc.

For another example, when the parameter sensed by the sensor 24 is pressure being applied by the jaws 20, 22 to tissue and/or other material grasped therebetween, the robotic surgical system can use the pressure data to adjust one or both of the jaws 20, 22 to adjust the amount of pressure being applied by the jaws 20, 22 so, e.g., the jaws 20, 22 more effectively grasp the tissue and/or other material and/or the jaws 20, 22 do not exceed a safe amount of pressure.

For yet another example, when the parameter sensed by the sensor 24 is a type of staple cartridge seated in the end effector 14, the robotic surgical system can use the cartridge type data to verify that the cartridge is compatible with the tool 10. If incompatibility is detected, the robotic surgical system can be configured to provide a warning to a user of the robotic surgical system, such as by providing a visual warning on a display of the robotic surgical system, so the user can address the problem. Additionally or alternatively, the robotic surgical system can use the cartridge type data in controlling deployment of staples from the cartridge, such as by providing an input to the tool 10 that allows a staple pusher of the tool 10 to translate enough of a longitudinal distance along the end effector 14 to deploy all of the staples from the cartridge.

For still another example, when the parameter sensed by the sensor 24 is presence of a staple cartridge within the end effector 14, the robotic surgical system can use the cartridge presence data as a safety check where the robotic surgical system cannot provide control signals to the tool 10 in response to user inputs to the robotic surgical system until the tool 10 is verified as having a staple cartridge present therein as indicated by the cartridge presence data. If the cartridge presence data indicates that a cartridge is not present (which may include a cartridge being entirely absent or a cartridge being improperly loaded into the end effector 14 and thus sensed as not being present), the robotic surgical system can be configured to provide a warning to a user of the robotic surgical system, such as by providing a visual warning on a display of the robotic surgical system, so the user can address the problem.

For another example, when the parameter sensed by the sensor 24 is impedance of tissue grasped by the jaws 20, 22, the robotic surgical system can use the impedance data to adjust various controls of the surgical tool 10, such as the amount of pressure being applied by the jaws 20, 22, an amount of energy being applied to the tissue, etc. Embodiments of impedance sensors and using sensed tissue impedance data are variously described in U.S. Pat. Pub. No. 2012/0292367 entitled "Robotically-Controlled End Effector" filed Feb. 13, 2012, U.S. Pat. Pub. No. 2015/0209059 entitled "Methods And Devices For Controlling Motorized Surgical Devices" filed Jan. 28, 2014, U.S. Pat. No. 5,558,671 entitled "Impedance Feedback Monitor For Electrosurgical Instrument" filed Sep. 24, 1996, U.S. Pat. Pub. No. 2015/0209573 entitled "Surgical Devices Having Controlled Tissue Cutting And Sealing" filed Jan. 28, 2014, and U.S. patent application Ser. No. 15/689,072 entitled "Methods, Systems, And Devices For Controlling Electrosurgical Tools" filed Aug. 29, 2017, which are hereby incorporated by reference in their entireties.

For still another example, when the parameter sensed by the sensor 24 is position of a cutting element relative to the end effector 14, the robotic surgical system can use the position data to adjust various controls of the surgical tool 10, such as to adjust a speed of the cutting element's translation and/or to adjust an amount of energy being applied by the tool 10 to tissue grasped by the end effector 14.

For yet another example, when the parameter sensed by the sensor 24 is angle of the end effector's jaws 20, 22, the robotic surgical system can use the angle data to adjust various controls of the surgical tool 10, such as to allow cutting element translation, staple firing, and/or energy application only when the angle indicates that the jaws 20, 22 are closed.

Embodiments of position sensors (e.g., a Hall Effect sensor) to determine cutting element position along an end effector, embodiments of load sensors (e.g., a pressure sensor) to determine closure pressure force exerted by an end effector, embodiments of force sensors, embodiments of sensors (e.g., a position switch, a Hall Effect sensor, or an optical sensor) to determine an angle of the end effector's closure, and embodiments of impedance sensors to measure impedance of clamped tissue are variously described in U.S. Pat. Pub. No. 2012/0292367 entitled "Robotically-Controlled End Effector" filed Feb. 13, 2012, U.S. Pat. Pub. No. 2015/0209059 entitled "Methods And Devices For Controlling Motorized Surgical Devices" filed Jan. 28, 2014, U.S. Pat. No. 5,558,671 entitled "Impedance Feedback Monitor For Electrosurgical Instrument" filed Sep. 24, 1996, and U.S. Pat. Pub. No. 2015/0209573 entitled "Surgical Devices Having Controlled Tissue Cutting And Sealing" filed Jan. 28, 2014, which are hereby incorporated by reference in their entireties.

The wrist 16 of the surgical tool 10 can have any of a variety of configurations. Exemplary embodiments of a wrist of a surgical tool and of effecting articulation at the wrist are described in International Pat. Pub. No. WO 2014/151952 entitled "Compact Robotic Wrist" filed on Mar. 13, 2014, International Pat. Pub. No. WO 2014/151621 entitled "Hyperdexterous Surgical System" filed on Mar. 13, 2014, U.S. Pat. Pub. No. 2018/0000543 entitled "Methods, Systems, And Devices For Initializing A Surgical Tool" filed on Jul. 1, 2016, and U.S. patent application Ser. No. 15/237,648 entitled "Methods, Systems, And Devices For Causing End Effector Motion With A Robotic Surgical System" filed on Aug. 16, 2016, which are hereby incorporated by reference in their entireties. In general, the wrist 16 can include a joint configured to allow movement of the end effector 14 relative to the shaft 12, such as a pivot joint at which the jaws 20, 22 are pivotally attached. In some embodiments, the pivoting motion can include pitch movement about a first axis of the wrist 16 (e.g., a X axis), yaw movement about a second axis of the wrist 16 (e.g., a Y axis), and combinations thereof to allow for 360° rotational movement of the end effector 14 about the wrist 16. In other embodiments, the pivoting motion can be limited to movement in a single plane, e.g., only pitch movement about the first axis of the wrist 16 or only yaw movement about the second axis of the wrist 16, such that end effector 14 rotates in a single plane.

The tool housing 18 can have any of a variety of configurations. In general, the tool housing 18 includes one or more actuation mechanisms at least partially disposed therein configured to cause movement of the end effector 14 about the wrist 16. The one or more actuation mechanisms can include, for example, one or more movement mechanisms, such as pulley(s), rotors, etc., operably coupled to a plurality of flexible members, e.g., cables, cords, etc., extending along the shaft 12 and configured to be moved to cause translation of the flexible members. The tool housing 18 is configured to be releasably attached to a robotic surgical system (also referred to herein as a "robot" or "surgical robot") so as to releasably attach the tool 10 to the robot. The tool housing 18 can be configured to releasably attach to a robot in any of a variety of ways, as will be appreciated by a person skilled in the art, such as by clamping thereto, clipping thereto, or slidably mating therewith. The one or more movement mechanisms are configured to be controlled by the robot, as will be appreciated by a person skilled in the art, such as by the robot including one or more motors operably coupled to one or more inputs of the tool housing 18 that are operably coupled to the one or more movement mechanisms. The robot includes a computer system that can receive user inputs and can control the motor(s) in response to the user inputs and hence control movement of the flexible members and consequently the end effector 14.

Figure 3:
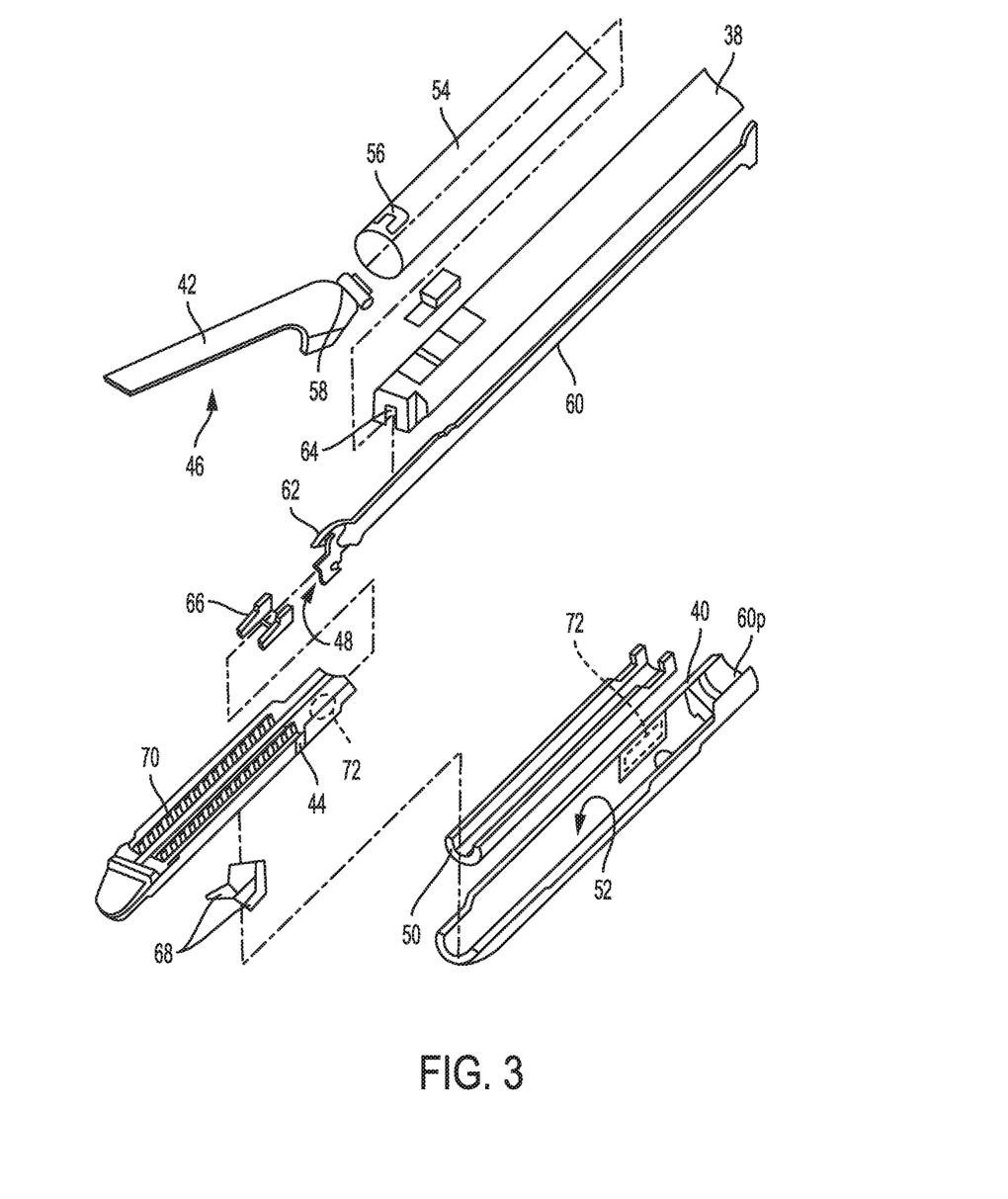
FIG. 3 is an exploded view of a distal portion of another embodiment of a surgical tool.

In at least some embodiments, the surgical tool 10 can be a stapler, as mentioned above. FIG. 3 illustrates a distal portion of one embodiment of a surgical stapling tool. The stapler includes an elongate shaft 38 and an end effector at a distal end of the shaft 38. A tool housing (not shown) is at a proximal end of the shaft 38, as discussed herein. The end effector in this illustrated embodiment includes opposed lower and upper jaws 40, 42. The lower jaw 40 includes a staple channel configured to support a staple cartridge 44, and the upper jaw 42 has an anvil surface 46 that faces the lower jaw 40 and is configured to operate as an anvil to help deploy staples of the staple cartridge 44 (the staples are obscured in FIG. 3). At least one of the lower and upper jaws 40, 42 is moveable relative to the other of the lower and upper jaws 40, 42 to clamp tissue and/or other material disposed therebetween. In at least some embodiments, one of the lower and upper jaws 40, 42 can be fixed or otherwise immovable. In some other embodiments, both of the lower and upper jaws 40, 42 be movable. Components of a firing system can be configured to pass through at least a portion of the end effector to eject the staples into the clamped tissue. A cutting element 48, which is a knife blade in this illustrated embodiment, can be associated with the firing system to cut tissue during a stapling procedure.

In this illustrated embodiment, the lower jaw 40 serves as a cartridge assembly or carrier, and the upper jaw 42 serves as an anvil. The staple cartridge 44 is supported in a staple tray 50, which in turn is supported within a cartridge channel 52 of the lower jaw 40. The upper jaw 42 has a plurality of staple forming pockets (obscured in FIG. 3), each of which is positioned above a corresponding staple from the plurality of staples contained within the staple cartridge 44.

Various clamping components can be used to effect opening and closing of the jaws 40, 42 to selectively clamp tissue therebetween. A closure tube 54, whose distal end includes a horseshoe aperture 56 that engages a closure feature 58 of the upper jaw 42, selectively imparts an opening motion to the upper jaw 42 during proximal longitudinal motion and a closing motion to the upper jaw 42 during distal longitudinal motion of the closure tube 42 in response to input from the tool driver operatively coupled thereto. As mentioned above, the opening and closure of the end effector may be effected by relative motion of the lower jaw 40 with respect to the upper jaw 42, relative motion of the upper jaw 42 with respect to the lower jaw 40, or by motion of both jaws 40, 42 with respect to one another.

The firing components of the illustrated embodiment includes a firing bar 60, which has an E-beam 62 on a distal end thereof. The E-beam 62 has the cutting element 48 at its distal end. The firing bar 60 is flexible in at least a distal portion thereof to facilitate bending of the firing bar 60 at the wrist where the end effector is articulated. The firing bar 60 is disposed within the shaft 38, for example in a longitudinal firing bar slot 64 of the shaft 38, and guided by a firing input received by the stapler from a tool driver coupled thereto. The firing input can cause distal motion of the E-beam 62 through at least a portion of the end effector to thereby cause the firing of staples contained within the staple cartridge 44. As in this illustrated embodiment, guides projecting from a distal end of the E-Beam 62 engage a sled 66, which in turn can push staple drivers 68 upwardly through staple cavities 70 formed in the staple cartridge 44. Upward movement of the staple drivers 68 applies an upward force on each of the plurality of staples within the cartridge 44 to thereby push the staples upwardly against the anvil surface 46 of the upper jaw 42 and create formed staples.

The end effector can include a sensor 72 as described herein. The sensor 72 can be, for example, in the cartridge 44 that is seated in the lower jaw 40. For another example, the sensor 72 can be in the lower jaw 40. The sensor's location as shown in each of the cartridge 44 and lower jaw 40 in this illustrated embodiment are examples only, and the sensor can be located elsewhere in the cartridge 44 and lower jaw 40. In an embodiment that includes multiple sensors, each of the cartridge 44 and the lower jaw 40 can include a sensor. The sensor can be in a variety of other locations, such as in the upper jaw 42 or the staple tray 50.

Various embodiments of surgical staplers and uses thereof are further described in U.S. Pat. Pub. No. 2013/0256377 entitled "Layer Comprising Deployable Attachment Members" filed Feb. 8, 2013, U.S. Pat. No. 8,393,514 entitled "Selectively Orientable Implantable Fastener Cartridge" filed Sep. 30, 2010, U.S. Pat. No. 8,317,070 entitled "Surgical Stapling Devices That Produce Formed Staples Having Different Lengths" filed Feb. 28, 2007, U.S. Pat. No. 7,143,925 entitled "Surgical Instrument Incorporating EAP Blocking Lockout Mechanism" filed Jun. 21, 2005, U.S. Pat. Pub. No. 2015/0134077 entitled "Sealing Materials For Use In Surgical Stapling" filed Nov. 8, 2013, U.S. Pat. Pub. No. 2015/0134076, entitled "Hybrid Adjunct Materials for Use in Surgical Stapling" filed Nov. 8, 2013, U.S. Pat. Pub. No. 2015/0133996 entitled "Positively Charged Implantable Materials and Method of Forming the Same" filed Nov. 8, 2013, U.S. Pat. Pub. No. 2015/0129634 entitled "Tissue Ingrowth Materials and Method of Using the Same" filed Nov. 8, 2013, U.S. Pat. Pub. No. 2015/0133995 entitled "Hybrid Adjunct Materials for Use in Surgical Stapling" filed Nov. 8, 2013, U.S. Pat. Pub. No. 2015/0272575 entitled "Surgical Instrument Comprising a Sensor System" filed Mar. 26, 2014, U.S. Pat. Pub. No. 2015/0351758 entitled "Adjunct Materials and Methods of Using Same in Surgical Methods for Tissue Sealing" filed Jun. 10, 2014, and U.S. patent application Ser. No. 15/422,740 entitled "Resisting Torque In Articulating Surgical Tools" filed Feb. 2, 2017, which are hereby incorporated by reference in their entireties.

As will be appreciated by a person skilled in the art, electronic communication between various integral components of and components removably connected to a robotic surgical system can be wired or wireless. A person skilled in the art will also appreciate that all electronic communication in the robotic surgical system can be wired, all electronic communication in the robotic surgical system can be wireless, or some portions of the robotic surgical system can be in wired communication and other portions of the system can be in wireless communication.

Figure 4:
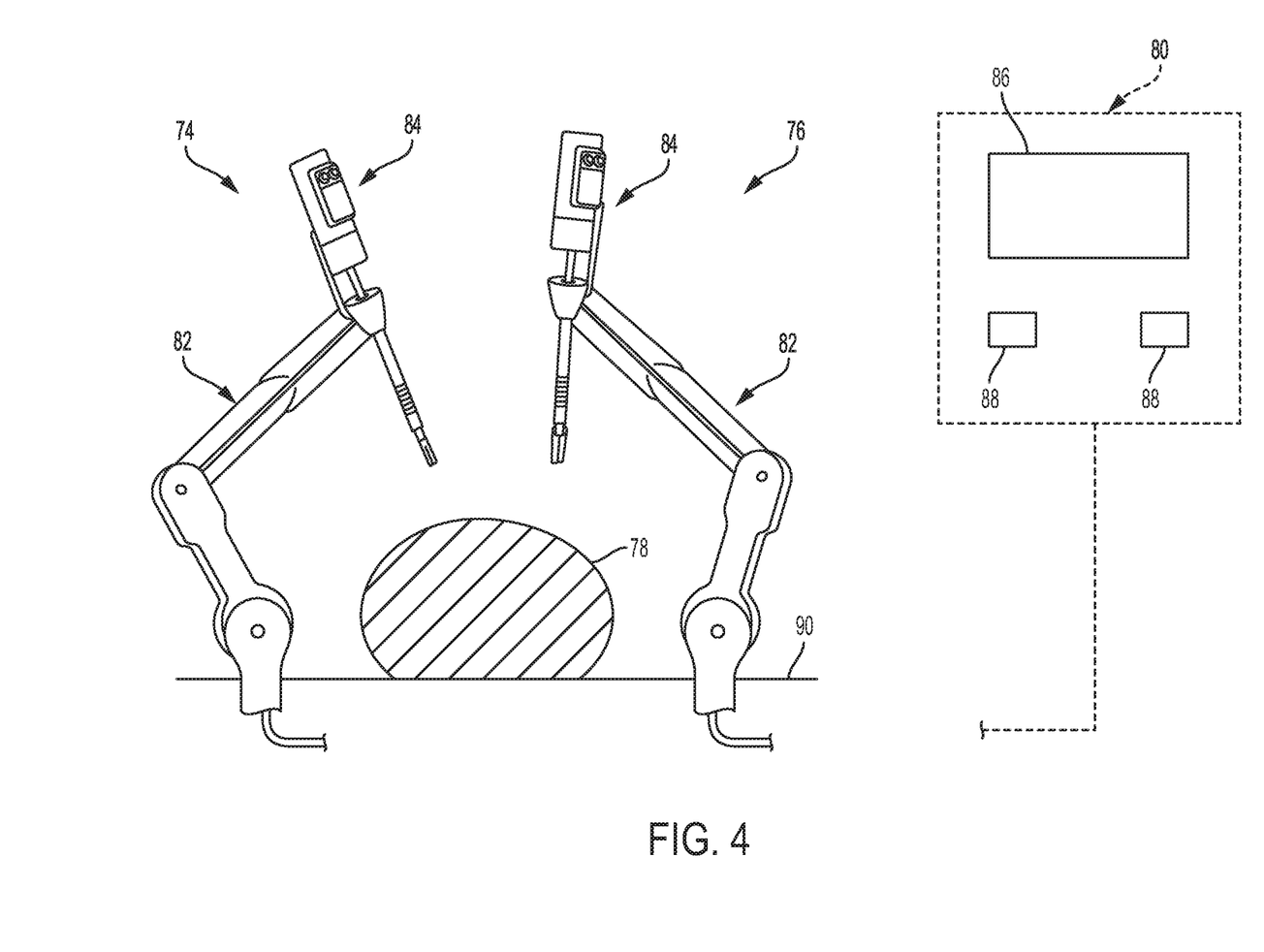
FIG. 4 is a perspective view of one embodiment of a robotic surgical system that includes a patient-side portion and a user-side portion.

FIG. 4 is a perspective view of one embodiment of a robotic surgical system 74 that includes a patient-side portion 76 that is positioned adjacent to a patient 78, and a user-side portion 80 that is located a distance from the patient, either in the same room and/or in a remote location. The patient-side portion 76 generally includes one or more robotic arms 82 and one or more tool assemblies 84 that are configured to releasably couple to a robotic arm 82. The user-side portion 76 generally includes a vision system 86 for viewing the patient 78 and/or surgical site, and a control system 88 for controlling the movement of the robotic arms 108 and each tool assembly 84 during a surgical procedure.

The control system 88 can have a variety of configurations and can be located adjacent to the patient (e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 88 can include components that enable a user to view a surgical site of the patient 78 being operated on by the patient-side portion 76 and/or to control one or more parts of the patient-side portion 76 (e.g., to perform a surgical procedure at the surgical site). In some embodiments, the control system 88 can also include one or more manually-operated input devices, such as a joystick, exoskeletal glove, a powered and gravity-compensated manipulator, or the like. The one or more input devices can control teleoperated motors which, in turn, control the movement of the surgical system, including the robotic arms 82 and tool assemblies 84.

The patient-side portion 76 can have a variety of configurations. As illustrated in FIG. 4, the patient-side portion 76 can couple to an operating table 90. However, in other embodiments, the patient-side portion 76 can be mounted to a wall, to the ceiling, to the floor, or to other operating room equipment. Further, while the patient-side portion 76 is shown as including two robotic arms 82, more or fewer robotic arms 82 may be included. Furthermore, the patient-side portion 76 can include separate robotic arms 82 mounted in various positions, such as relative to the surgical table 90 (as shown in FIG. 4). Alternatively, the patient-side portion 76 can include a single assembly that includes one or more robotic arms 82 extending therefrom.

Figure 5:
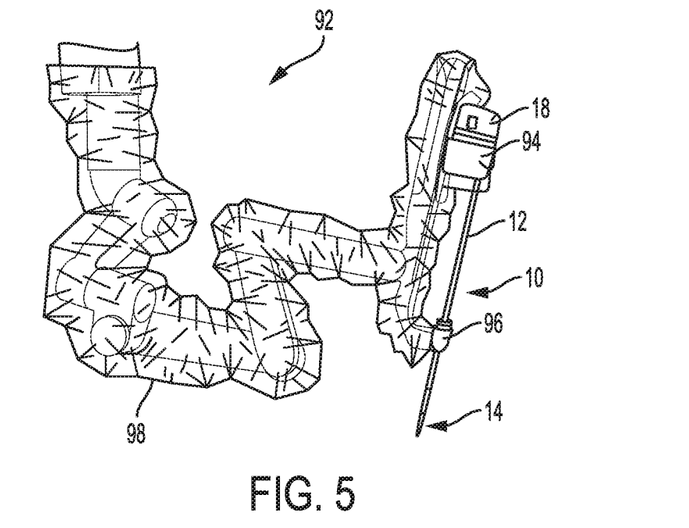
FIG. 5 is a perspective view of one embodiment of a robotic arm of a robotic surgical system with the surgical tool of FIG. 1 releasably and replaceably coupled to the robotic arm.

FIG. 5 illustrates another embodiment of a robotic arm 92 and the surgical tool 10 of FIG. 1 releasably and replaceably coupled to the robotic arm 92, although other surgical tools can be similarly releasably and replaceably coupled thereto. The robotic arm 92 is configured to support and move the associated tool 10 along one or more degrees of freedom (e.g., all six Cartesian degrees of freedom, five or fewer Cartesian degrees of freedom, etc.).

The robotic arm 92 includes a tool driver 94 at a distal end of the robotic arm 92, which can assist with controlling features associated with the tool 10. The robotic arm 92 also includes an entry guide 96 (e.g., a cannula mount, cannula, etc.) that can be a part of or releasably and replaceably coupled to the robotic arm 92, as shown in FIG. 5. A shaft of a tool assembly can be inserted through the entry guide 96 for insertion into a patient, as shown in FIG. 5 in which the shaft 12 of the tool 10 of FIG. 1 is shown inserted through the entry guide 96.

In order to provide a sterile operation area while using the surgical system, a barrier 98 can be placed between the actuating portion of the surgical system (e.g., the robotic arm 92) and the surgical instruments coupled thereto (e.g., the tool 10, etc.). A sterile component, such as an instrument sterile adapter (ISA), can also be placed at the connecting interface between the tool 10 and the robotic arm 92. The placement of an ISA between the tool 10 and the robotic arm 92 can ensure a sterile coupling point for the tool 10 and the robotic arm 92. This permits removal of surgical instruments from the robotic arm 92 to exchange with other surgical instruments during the course of a surgery without compromising the sterile surgical field.

Figure 6:
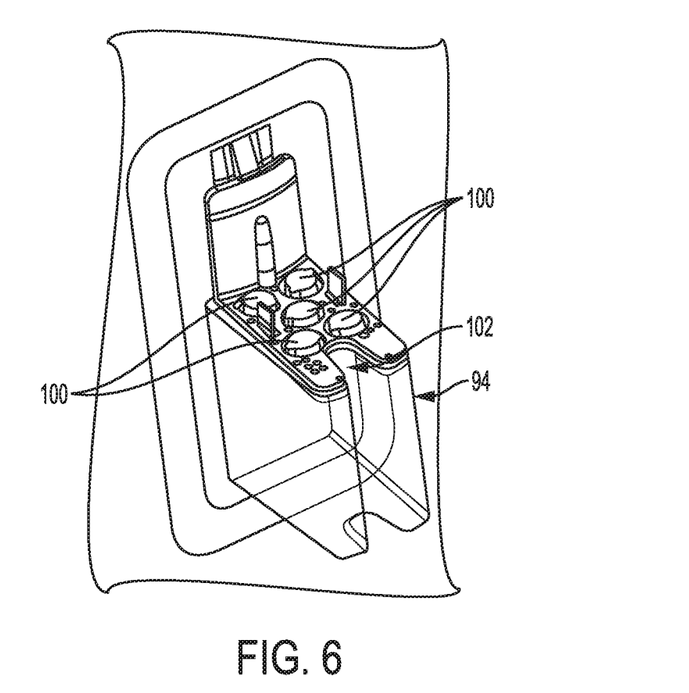
FIG. 6 is a perspective view of a tool driver of the robotic arm of FIG. 5.

FIG. 6 illustrates the tool driver 94 in more detail. As shown, the tool driver 94 includes one or more motors, e.g., five motors 100 are shown, that control a variety of movements and actions associated with the tool 10 coupled to the arm 92. For example, each motor 100 can couple to and/or interact with an activation feature (e.g., gear) associated with the tool 10 for controlling one or more actions and movements that can be performed by the tool 10, such as for assisting with performing a surgical operation. The motors 100 are accessible on the upper surface of the tool driver 94, and thus the tool 10 (e.g., the housing 18 thereof) is configured to mount on top of the tool driver 94 to couple thereto. Exemplary embodiments of motor operation and components of a tool housing (also referred to as a "puck") configured to controlled by tool driver motors are further described in previously mentioned International Pat. Pub. No. WO 2014/151952 entitled "Compact Robotic Wrist" filed Mar. 13, 2014 and International Pat. Pub. No. WO 2014/151621 entitled "Hyperdexterous Surgical System" filed Mar. 13, 2014, U.S. Pat. Pub. No. 2018/0000543 entitled "Methods, Systems, And Devices For Initializing A Surgical Tool" filed Jul. 1, 2016, and in U.S. patent application Ser. No. 15/237,653 entitled "Methods, Systems, And Devices For Controlling A Motor Of A Robotic Surgical Systems" filed Aug. 16, 2016, which is hereby incorporated by reference in its entirety.

The tool driver 94 also includes a shaft-receiving channel 102 formed in a sidewall thereof for receiving a tool shaft, e.g., the shaft 12 of the tool 10. In other embodiments, the shaft can extend through an opening in the tool driver 122, or the two components can mate in various other configurations.

FIG. 2 illustrates one embodiment of use of a surgical tool that has a sensor configured to sense a parameter related to the surgical tool and to wirelessly communicate the sensed data to another device. Although the use of FIG. 2 is discussed with respect to the surgical tool 10 of FIG. 1 and the robotic surgical system 74 of FIG. 4, any of the surgical tools and robotic surgical systems described herein can be similarly used. Additionally, the other surgical tool 26 in the illustrated embodiment of FIG. 2 is an endoscopic camera, but as mentioned above, another type of device can be used to communicate with the surgical tool and with the robotic surgical system.

As shown in FIG. 2, distal portions of each of the surgical tool 10 and second surgical tool 26 have been advanced through tissue 11 of a patient, e.g., through the patient's body wall, to be located within a body cavity 13 of the patient. The shaft 12 of the surgical tool 10 has been advanced through an entry guide 15 that extends through the tissue 11 and, as discussed above, can be a part of or releasably and replaceably coupled to the robotic surgical system 74. Similarly, the shaft 36 of the second surgical tool 26 has been advanced through a second entry guide 17.

As shown by the wireless signal lines 30 in FIG. 2, the surgical tool's sensor 24 transmits sensed data to the second tool 26, e.g., the communication mechanism 32 thereof. The sensed data transmission can be according to any of a variety of schedules that may be pre-programmed into or otherwise controlled by the robotic surgical system 74, e.g., by the control system 88 thereof. For example, the sensor 24 can continuously sense data and continuously transmit sensed data to the second surgical tool 26. For another example, the sensor 24 can sense and transmit data every "X" amount of time, where "X" can have a variety of values, such as five seconds, ten seconds, thirty seconds, one minute, etc. For yet another example, the sensor 24 can sense and transmit data on demand as controlled by the robotic surgical system 74.

FIG. 2 shows only one surgical tool 10 that communicates with the second surgical tool 26 within the body cavity 13, but one or more additional surgical tools can similarly communicate with the second surgical tool 26. The one or more additional surgical tools can be disposed within the body cavity 13 simultaneously or sequentially with the surgical tool 10.

In the illustrated embodiment of FIG. 2, the other surgical tool 26 does not include a sensor configured to sense a parameter related to the other surgical tool 26 and to wirelessly communicate that sensed data to another device configured to transmit the sensed data to a robotic surgical system. In other embodiments, the other surgical tool 26 (or other similar surgical tool as described herein) to which the surgical tool 10 (or other similar surgical tool described herein) wirelessly transmits data can include such a sensor, e.g., a sensor similar to the sensor 24 of the tool 10 of FIG. 2. The other surgical tool can thus be configured to transmit data sensed via its own sensor to the robotic surgical system and to transmit to the robotic surgical system data received from the surgical tool 10 and/or from other surgical tools from which the other surgical tool wirelessly receives data.

In the illustrated embodiment of FIGS. 1 and 2, the surgical tool 10 does not include a wired connection with a robotic surgical system which could be used transmit data sensed by the sensor 24 to the robotic surgical system. In other embodiments, the surgical tool 10 can include such a wired connection, e.g., by including a wire extending along its elongate shaft 12 similar to the wire 34 that extends along the elongate shaft 36 of the second surgical tool 26 of FIG. 2. Such a surgical tool can thus have redundant capability to communicate data to the robotic surgical system via the wired connection and via the tool's wireless communication of the data to another surgical tool. Redundancy may help ensure that the robotic surgical system receives critical data in the event that the wireless communication of data from the surgical tool fails, such as because of signal data loss, because of removal of the other surgical tool from the patient's body during the surgical procedure for cleaning or other reason, or because of another problem with the wireless communication. The redundancy can be achieved by the surgical tool being configured to transmit the sensed data to the robotic surgical system via its own wired connection and the surgical tool being configured to wirelessly transmit sensed data to the other surgical tool for transmission to the robotic surgical system via the other surgical tool's wired connection to the robotic surgical system. The data transmitted to the robotic surgical system from the surgical tool and/or the other surgical tool can be identified to the robotic surgical system as being possibly redundantly received data so the robotic surgical system does not confuse the same sensed data as being two different sets of sensed data, such as by the data received by the robotic surgical system including time stamp data indicative of when the data was sensed by the surgical tool so the robotic surgical system can identify data as being redundant by having matching time stamps.

In embodiments in which multiple surgical tools disposed in a patient's body are each configured to wirelessly transmit sensed data to another surgical tool for communication to a robotic surgical system, any one or more of the multiple surgical tools can include a wired connection for redundancy.

As discussed above, the control systems disclosed herein can be implemented using one or more computer systems, which may also be referred to herein as digital data processing systems and programmable systems.

One or more aspects or features of the control systems described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

Figure 7:
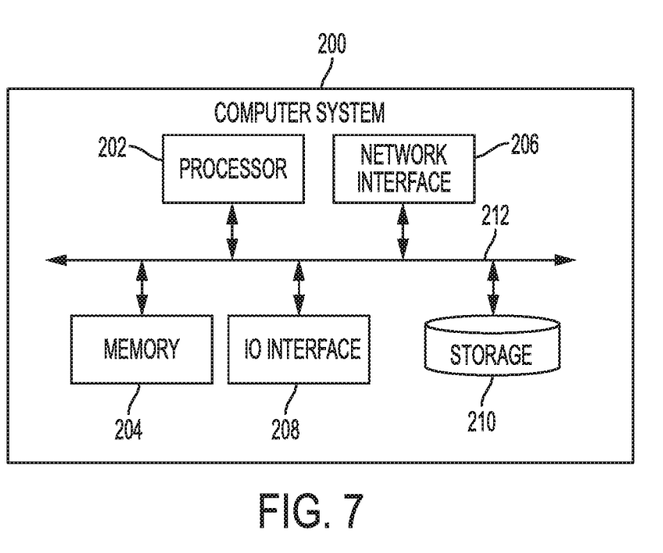
FIG. 7 is a schematic view of one embodiment of a computer system.

FIG. 7 illustrates one exemplary embodiment of a computer system 200. As shown, the computer system 200 includes one or more processors 202 which can control the operation of the computer system 200. "Processors" are also referred to herein as "controllers." The processor(s) 202 can include any type of microprocessor or central processing unit (CPU), including programmable general-purpose or special-purpose microprocessors and/or any one of a variety of proprietary or commercially available single or multi-processor systems. The computer system 200 can also include one or more memories 204, which can provide temporary storage for code to be executed by the processor(s) 202 or for data acquired from one or more users, storage devices, and/or databases. The memory 204 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 200 can be coupled to a bus system 212. The illustrated bus system 212 is an abstraction that represents any one or more separate physical busses, communication lines/interfaces, and/or multi-drop or point-to-point connections, connected by appropriate bridges, adapters, and/or controllers. The computer system 200 can also include one or more network interface(s) 206 that enable the computer system 200 to communicate with remote devices, e.g., motor(s) coupled to the drive system that is located within the surgical device or a robotic surgical system, one or more input/output (IO) interface(s) 208 that can include one or more interface components to connect the computer system 200 with other electronic equipment, such as sensors located on the motor (s), and one or more storage device(s) 210. The storage device(s) 210 can include any conventional medium for storing data in a non-volatile and/or non-transient manner. The storage device(s) 210 can thus hold data and/or instructions in a persistent state, i.e., the value(s) are retained despite interruption of power to the computer system 200.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

A person skilled in the art will appreciate that the present invention has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
a surgical tool including an elongate shaft having an end effector at a distal end thereof, the end effector being configured to be disposed within a body of a patient, the surgical tool being configured to releasably and replaceably couple to a robotic surgical system configured to provide a control signal to the surgical tool to allow the end effector to perform a function, the surgical tool including a sensor at the end effector, the sensor being configured to sense a parameter associated with the surgical tool, and the sensor being configured to wirelessly transmit a signal indicative of the sensed parameter to a second surgical tool disposed within the body of the patient and releasably and replaceably coupled to the robotic surgical system.

2. The system of claim 1, wherein the parameter associated with the surgical tool includes at least one of force, pressure, type of a staple cartridge seated in the end effector, presence of a staple cartridge within the end effector, impedance of tissue engaged by the end effector, position of a cutting element of the surgical tool relative to the end effector, and angle of the end effector relative to the elongate shaft.

3. The system of claim 1, wherein the function includes at least one of closing the end effector, opening the end effector, articulating the end effector relative to the elongate shaft, rotating the end effector relative to the elongate shaft, rotating the end effector and the elongate shaft as a unit about a longitudinal axis of the elongate shaft, ejecting staples from the end effector, and applying energy to tissue engaged by the end effector.

4. The system of claim 1, further comprising the second surgical tool configured to be disposed within the body of the patient and configured to releasably and replaceably couple to the robotic surgical system, the second surgical tool including a communication mechanism configured to receive the signal from the sensor, and the second surgical tool being configured to transmit a second signal indicative of the signal to the robotic surgical system.

5. The system of claim 4, wherein the communication mechanism includes a transceiver, and the second surgical tool includes a wire operatively connected to the communication mechanism, extending along an elongate shaft of the second surgical tool, and configured to communicate the second signal.

6. The system of claim 4, wherein the communication mechanism includes an antenna, and the second surgical tool includes a circuit board configured to process the signal received by the antenna into the second signal.

7. The system of claim 4, wherein the second surgical tool includes a camera.

8. The system of claim 4, further comprising a control system of the robotic surgical system configured to receive the second signal from the second surgical tool, the control system being configured to use the second signal to generate the control signal.

9. A surgical system, comprising:
a first surgical tool including an elongate shaft having an end effector at a distal end thereof, the end effector being configured to be disposed within a body of a patient, the surgical tool being configured to releasably and replaceably couple to a robotic surgical system configured to provide a control signal to the surgical tool to allow the end effector to perform a function, the surgical tool including a sensor at the end effector, the sensor being configured to sense a parameter associated with the surgical tool; and
a second surgical tool configured to be disposed within the body of the patient and to be releasably and replaceably coupled to the robotic surgical system, the second surgical tool being configured to wirelessly receive a first signal from the first surgical tool that is indicative of the sensed parameter, and the second surgical tool being configured to transmit a second signal indicative of the first signal to the robotic surgical system.

10. The system of claim 9, wherein the parameter associated with the first surgical tool includes at least one of force, pressure, type of a staple cartridge seated in the end effector, presence of a staple cartridge within the end effector, impedance of tissue engaged by the end effector, position of a cutting element of the surgical tool relative to the end effector, and angle of the end effector relative to the elongate shaft.

11. The system of claim 9, wherein the function includes at least one of closing the end effector, opening the end effector, articulating the end effector relative to the elongate shaft, rotating the end effector relative to the elongate shaft, rotating the end effector and the elongate shaft as a unit about a longitudinal axis of the elongate shaft, ejecting staples from the end effector, and applying energy to tissue engaged by the end effector.

12. The system of claim 9, wherein the second surgical tool includes a communication mechanism configured to receive the first signal from the first surgical tool, the communication mechanism including a transceiver.

13. The system of claim 9, wherein the second surgical tool includes a communication mechanism configured to receive the first signal from the first surgical tool, the communication mechanism including an antenna, and the second surgical tool includes a circuit board configured to process the signal received by the antenna into the second signal.

14. The system of claim 9, wherein the second surgical tool includes a camera.

15. The system of claim 9, further comprising a control system of the robotic surgical system configured to receive the second signal from the second surgical tool, the control system being configured to use the second signal to generate the control signal.

16. A surgical method, comprising:
positioning an end effector of a first surgical tool in a body of a patient, the first surgical tool being releasably and replaceably coupled to a robotic surgical system;
positioning a distal portion of a second surgical tool in the body of the patient, the second surgical tool being releasably and replaceably coupled to the robotic surgical system;
sensing a parameter associated with the first surgical tool with a sensor at the end effector of the first surgical tool;
wirelessly transmitting a first signal from the end effector of the first surgical tool to a communication mechanism at the distal portion of the second surgical tool, the first signal being indicative of the sensed parameter; and
transmitting a second signal from the second surgical tool to the robotic surgical system, the second signal being indicative of the first signal received by the second surgical tool.

17. The method of claim 16, further comprising transmitting a third signal from the robotic surgical system to the first surgical tool based on the second signal received by the robotic surgical system, the third signal including an instruction to the first surgical tool for performance of a function of the end effector.

18. The method of claim 17, wherein the function includes at least one of closing the end effector, opening the end effector, articulating the end effector relative to the elongate shaft, rotating the end effector relative to the elongate shaft, rotating the end effector and the elongate shaft as a unit about a longitudinal axis of the elongate shaft, ejecting staples from the end effector, and applying energy to tissue engaged by the end effector.

19. The method of claim 16, wherein the parameter associated with the first surgical tool includes at least one of force, pressure, type of a staple cartridge seated in the end effector, presence of a staple cartridge within the end effector, impedance of tissue engaged by the end effector, position of a cutting element of the surgical tool relative to the end effector, and angle of the end effector relative to the elongate shaft.

20. The method of claim 16, wherein the transmission of the second signal includes transmission of the second signal along a wire extending along an elongate shaft of the second surgical tool.

* * * * *